Figure 1:
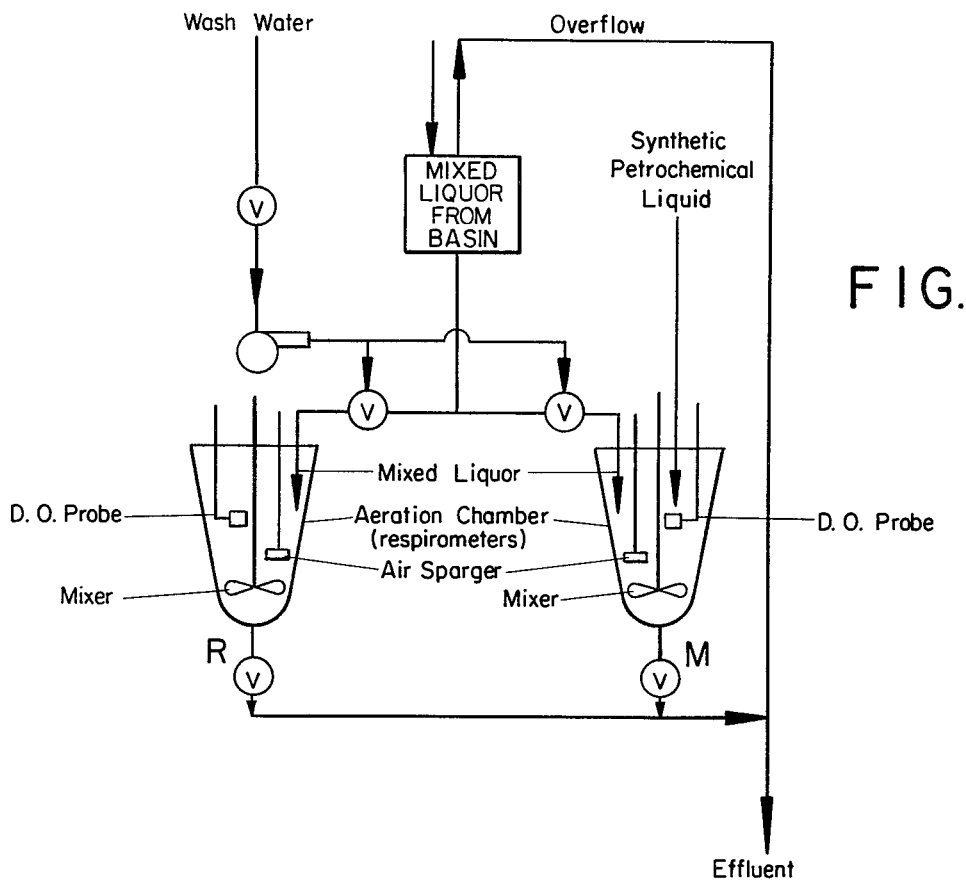

United States Patent [19]

McKenna

[11] 4,329,232

[45] May 11, 1982

[54] METHOD FOR MEASURING BIOMASS VIABILITY

[75] Inventor: Eva J. McKenna, Charleston, W. Va.

[73] Assignee: Union Carbide Corporation, Danbury, Conn.

[21] Appl. No.: 214,585

[22] Filed: Dec. 9, 1980

[51] Int. Cl.³ .............................................. C02F 3/02
[52] U.S. Cl. .................................. 210/614; 210/620; 23/230 B
[58] Field of Search ............. 210/614, 620, 739, 96.1; 435/291, 818; 422/79; 23/230 B, 906

[56] References Cited

U.S. PATENT DOCUMENTS 3,723,255  3/1973  Walden et al. .................. 210/614 X
3,986,932  10/1976  Brushwyler et al. ............ 210/614 X
4,260,490  4/1981  Moss et al. ......................... 210/620

Primary Examiner—Thomas G. Wyse
Attorney, Agent, or Firm—Gerald R. O'Brien, Jr.

[57] ABSTRACT

A method is disclosed for measuring viability of a waste treatment basin biomass contained in a waste basin mixed liquor comprising measuring the rate of oxygen uptake in a first sample of said waste basin liquor; measuring the rate of oxygen uptake in a mixture of a second sample of said waste basin liquor and a sample of synthetic petrochemical reference liquid; subtracting to determine the differential of said rates; and effecting, by predetermined correlation with differential oxygen uptake rate, a determination of the viability of said biomass based on said differential oxygen uptake rate for said waste basin liquor.

5 Claims, 2 Drawing Figures

METHOD FOR MEASURING BIOMASS VIABILITY

The present invention relates to a method for measuring the viability of a waste treatment basin biomass contained in a waste basin mixed liquor.

A rapid means for determining the viable organism content of a system would be a valuable aid to process monitoring and control in, for example, industrial fermentation processes and secondary (biological) wastewater treatment.

In the area of aerobic wastewater treatment, viable biomass can be a more realistic basis than total organism content to:

Calculate organic loading (F/M where M is viable biomass and F is "food" or organic material);

Develop a biomass wasting strategy;

Formulate anticipatory control of aeration;

Achieve a more economical treatment plant design (based on biokinetic coefficient derived from viable biomass measurements).

Current methods employed to evaluate biomass viability include: (1) measurement of a chemical component (e.g. adenosine triphosphate) or enzymatic activity (e.g. dehydrogenase) present in living cells but absent in dead biomass; (2) direct count of living cells carried out in Petri dishes by spread or pour plate method, by membrane method or by vital staining with fluorochrome dyes; (3) most probable number (statistical) tube method. Measurement of a cellular chemical component or enzymatic activity and vital staining techniques require a skilled operator. In addition, cell culture methods require several days for growth to be expressed.

Biomass respiration (oxgyen uptake rate, i.e., OUR) of laboratory and pilot reactors and of waste treatment plant recycle sludge also has been used as a measure of cell viability. The disadvantages of this method as practiced will be discussed below. Another procedure employed a dilution technique to study relative biomass activities as measured by substrate dependent OUR, but no correlation with viable cell count was studied.

In the practice of the invention, a suspension of the biomass to be tested is aerated until the dissolved oxygen (D.O.) level reaches a predetermined level such as 6 mg $O_2$/l and then the OUR is determined by measuring the decrease of residual dissolved oxygen as a function of time by means of a suitable apparatus such as a polarographic membrane type probe (e.g. Yellow Springs Instrument). This rate is expressed on a biomass dry weight basis as mg $O_2$ per gram volatile suspended solids (gVSS) per hr, and is referred to as the reference OUR (REF OUR). Another biomass sample is aerated as above, and the OUR is measured in the presence of a saturating level of a standard substrate. This is a key aspect of the invention. The substrate-dependent rate is calculated as the difference between the latter and former rates and is designed as the difference OUR (DIFF OUR).

Biomass respiration is then correlated with viable cell count (colony forming units or CFU/gVSS) determined by standard spread plate technique. DIFF OUR and CFU/gVSS are determined on samples of varying viability from a given source and CFU/gVSS is plotted as a function of DIFF OUR where samples of waste activated sludge from a plant treating industrial wastewater were tested as above. From the graph or mathematical model the viability CFU/gVSS of the other biomass samples from the same source can be estimated from the DIFF OUR of the sample. If a sizeable variation in temperature is anticipated, the model should be evaluated for temperature effects and a temperature term included, if necessary.

Thus, in accordance with the present invention, a method is provided for semi-continuously evaluating the viability of a biomass of a waste treatment basin, said biomass contained in a waste basin mixed liquor, comprising the steps of: (a) measuring the rate of oxygen uptake, R, in a first sample of said waste basin mixed liquor, said first sample having a predetermined volume and a predetermined dissolved oxygen content; (b) separately measuring the rate of oxygen uptake, M, in a mixture of a second sample of said waste basin mixed liquor and a sample of synthetic petrochemical reference liquid, said second sample having substantially the same volume and dissolved oxygen content as said first sample, said mixture constituting predominantly said second sample of said waste basin mixed liquor and a relatively small amount of said synthetic petrochemical reference liquid; (c) subtracting to determine the differential of said rates, M minus R, which represents the differential oxygen uptake rate of said waste basin mixed liquor in the presence of said synthetic petrochemical reference liquid; and (d) effecting, by predetermined correlation with differential oxygen uptake rate, a determination of the viability of said biomass based on said differential oxygen uptake rate for said waste basin mixed liquor.

The invention is best practiced by carrying out the differential (DIFF) OUR determination in an automated device that simultaneously estimates oxygen consumption in a reference vessel which receives a suspension of biomass but no other additions (REF OUR) and in a measuring vessel which received, in addition to the biomass suspension, a saturating level of a synthetic substrate (MEAS OUR). The (DIFF OUR) is then computed as (MEAS OUR)-REF OUR.

As employed herein, the term "synthetic petrochemical reference liquid" shall mean a liquid selected to contain organic compounds representative of those normally present in the influent stream passed to waste purification aeration basins. The components of the synthetic petrochemical reference liquid are selected to be representative so that they are materials known to be oxidizable by the mixed liquor employed.

The process of the invention is designed to work with a high water-based system as in the industrial (biological) waste basin liquor system and in industrial fermentation processes.

A device such as the biological monitor described by J. R. Moss, et al. in copending U.S. patent application Ser. No. 093,039, filed Nov. 9, 1979, issued Apr. 7,1981 as U.S. Pat. No. 4,260,490; and entitled Biological Monitor to Safeguard Water Purification Process from Toxicants is suitable for modification and adaptation to this purpose. The instrument computes the DIFF OUR, displays this value along with the MEAS OUR and REF OUR on a digital readout and records the information on a strip chart and/or prints these values on tape. One full cycle of operation requires approximately 20 minutes, a considerable time saving over the prior growth method (6 days). ATP and dehydrogenase assays require greater than one hour and approximately 50 minutes, respectively.

FIG. 1 of the drawing represents such a device in schematic form; and

Figure 2:
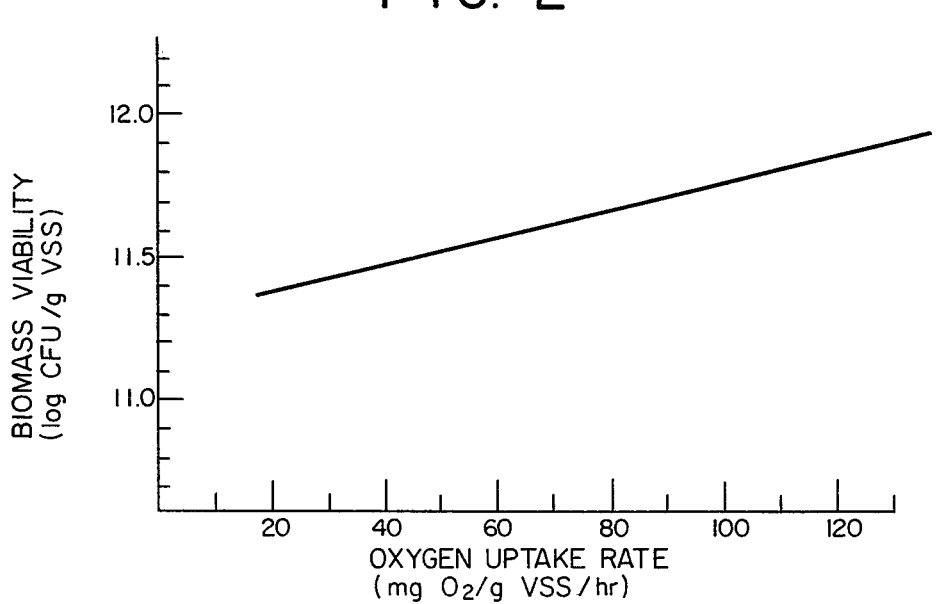

FIG. 2 of the drawing shows a plot of CFU/gVSS obtained by the spread plate method vs. DIFF OUR obtained with a biological monitor using activated sludge from the aeration basin of an industrial wastewater treatment plant.

It is to be understood that any commercial apparatus which will measure residual dissolved oxygen in the aqueous phase can be employed. In addition, a method for determining biomass viability must also be employed to establish the relationship for that biomass (i.e. between viability and dissolved oxygen uptake rate dependent on a synthetic feed); usable methods for establishing such viability include the pour plate method, membrane filter method, most probable number tube method and vital staining.

As practiced in the preferred method, the invention offers a rapid, semi-automatic method for biomass viability determination once the correlation between CFU/gVSS and DIFF OUR has been established for a given biomass.

In aerobic systems, where the organic stream quality also is of interest, the preferred method offers the economic advantage of determination of biomass viability as well as influent feed stream quality with a single instrument. Since the determination is rapid, the results represent a real-time measure and remedial action for process control can be taken in a timely fashion.

During times of poor process operation (e.g. in a wastewater treatment plant when effluent biochemical oxygen demand is high), correlation between CFU/gVSS and REF OUR (parameters used by the prior art to estimate biomass viability) is poor. In Example 1 the correlation coefficient for log CFU/gVSS vs DIFF OUR was 0.88 (significant at the 99% confidence level), while the correlation coefficient for log CFU/gVSS as a function of REF OUR was 0.15 (insignificant).

Apparatus suitable for carrying out the practice of the invention is shown schematically in FIG. 1 of the drawing. Referring specifically to the apparatus of FIG. 1, mixed liquor from the waste basin is fed through a holding tank, to both sides of the biological monitor shown, through the valves. An overflow of Effluent is also shown.

Between semi-continuous cycles of the use of biological monitor, wash water is employed and passed through the lines, valving means and pump to wash out both sides of the system to the Effluent waste.

On stabilized measurement of semi-continuous operation, the left-hand portion of the biological monitor operates to pass mixed liquor from the basin to the reference side of the measuring apparatus which is also charged with air, through the air sparger means, to the aeration chamber (respirometer). The fluid is mixed through use of the mixer, to effect homogeneity of the liquid on the reference side of the apparatus. A dissolved oxygen (D.O.) probe is employed to measure the dissolved oxygen uptake on the reference side of the apparatus. The fluids are then passed out of the reference side of the apparatus through a valving system to the Effluent waste line.

Simultaneously therewith, mixed liquor from the basin is passed into the measuring side of the apparatus into the aeration chamber (respirometer) into which is also passed synthetic petrochemical liquid. Air sparger and mixer means are also provided for the chamber on the measurement side and a dissolved oxygen probe of the type referred to in U.S. Pat. No. 4,260,490 is also employed. Discharge from the measurement side chamber passes through suitable valving means to a common Effluent discharge line to which the above-mentioned Overflow is also passed.

In the semi-continuous operation of the biological monitor in carrying out the process of the present invention, unreacted mixed liquor from the basin is passed into the reference side of the apparatus while mixed liquor from the basin, together with synthetic petrochemical liquid, is passed into the measuring side thereof. The resulting chemical reaction on the measurement side effects a change in the dissolved oxygen probe measurement from that obtained on the reference side of the apparatus and indicates the effect of the synthetic petrochemical liquid with the mixed liquor in increasing the oxygen uptake rate of the mixed liquor.

The electrical voltage generated in the dissolved oxygen (D.O. probe electrical takeoff from the measurement and reference cells) probes provides, in subtractive electrical circuit relationship, a differential voltage signal proportional to the M minus R reading which will vary from one semi-continuous operation to another.

With these values for semi-continuous M minus R (OUR) readings, one is provided with an oxygen uptake rate differential which is the DIFF OUR referred to hereinabove. These values are in the units of $mgO_2/gVSS/hr$ which corresponds to the base variable of the curve of that figure.

Then by referring to FIG. 2 of the drawing, a direct reference may be had between the DIFF OUR and the biomass viability, as expressed in log CFU/gVSS, which correspondingly appears on the vertical axis of that curve. Accordingly, one in possession of the relationship represented by such a curve is in position to readily translate M minus R values into biomass viability values.

It should be noted that the curve as set forth in FIG. 2 of the drawing is a curve expressed by the following relationship:

$$\log CFU/gVSS = 0.00483\ OUR_{CF} + 11.28$$

The following are examples of the process of the invention:

EXAMPLE 1

SOUTH CHARLESTON BIOMASS VIABILITY AS A FUNCTION OF CARBIDE FEED-DEPENDENT RESPIRATION

| Reactor | Date | CFU/ml[a] | MLVSS (g/l) | CFU/gVSS | Date | REF OUR[b] (mg $O_2$/l/hr) | DIFF OUR[b] (mg $O_2$/l/hr) | MLVSS (g/l) | REF OUR (mg $O_2$/g/ VSS/hr) | DIFF OUR (mg $O_2$/ gVSS/hr) |
|---|---|---|---|---|---|---|---|---|---|---|
| SAB | 4/29 | 2.7 × 10[8] | 4.34 | 6.2 × 10[10] | 4/26 | 46.5 | 207.9 | 4.04 | 11.5 | 51.5 |
| | 5/3 | 8.8 × 10[8] | 4.52 | 1.9 × 10[11] | 5/5 | 62.0 | 293.2 | 4.38 | 14.2 | 66.9 |
| | 5/10 | 6.1 × 10[8] | 3.46 | 1.8 × 10[11] | 5/9 | 16.4 | 271.6 | 3.82 | 4.3 | 71.1 |
| | 6/1 | 2.5 × 10[8] | 3.06 | 8.2 × 10[10] | 5/31 | 14.3 | 152.8 | 2.89 | 4.9 | 52.9 |
| | 6/23 | 4.9 × 10[8] | 3.52 | 1.4 × 10[11] | 6/24 | 14.5 | 248.3 | 3.48 | 4.2 | 71.4 |

EXAMPLE 1-continued

SOUTH CHARLESTON BIOMASS VIABILITY AS A FUNCTION OF CARBIDE FEED-DEPENDENT RESPIRATION

| Reactor | Date | CFU/ml[a] | MLVSS (g/l) | CFU/gVSS | Date | REF OUR[b] (mg O$_2$/l/hr) | DIFF OUR[b] (mg O$_2$/l/hr) | MLVSS (g/l) | REF OUR (mg O$_2$/g/VSS/hr) | DIFF OUR (mg O$_2$/gVSS/hr) |
|---|---|---|---|---|---|---|---|---|---|---|
| #1 | 4/29 | $2.9 \times 10^8$ | 4.80 | $6.0 \times 10^{10}$ | 4/26 | 39.5 | 251.5 | 3.96 | 10.0 | 63.5 |
|  | 5/3 | $4.0 \times 10^8$ | 5.10 | $7.8 \times 10^{10}$ | 5/5 | 35.4 | 324.6 | 5.04 | 7.0 | 64.4 |
|  | 5/10 | $2.4 \times 10^8$ | 4.82 | $5.0 \times 10^{10}$ | 5/12 | 35.8 | 353.0 | 5.28 | 6.8 | 66.9 |
|  | 6/1 | $1.7 \times 10^8$ | 2.02 | $8.4 \times 10^{10}$ | 5/31 | 81.0 | 114.0 | 2.36 | 34.3 | 48.3 |
|  | 6/23 | $2.9 \times 10^7$ | 3.92 | $7.9 \times 10^9$ | 6/24 | 29.7 | 100.2 | 4.20 | 7.1 | 23.9 |
| #2 | 4/29 | $6.6 \times 10^8$ | 4.52 | $1.5 \times 10^{11}$ | 4/26 | 111.8 | 350.2 | 4.36 | 25.6 | 80.3 |
|  | 5/3 | $1.2 \times 10^9$ | 3.42 | $3.5 \times 10^{11}$ | 5/5 | 67.4 | 291.4 | 3.52 | 19.1 | 82.8 |
|  | 5/10 | $4.9 \times 10^8$ | 3.64 | $1.3 \times 10^{11}$ | 5/12 | 140.7 | 173.1 | 3.00 | 46.9 | 57.7 |
|  | 6/1 | $1.6 \times 10^9$ | 3.60 | $4.4 \times 10^{11}$ | 5/31 | 25.4 | 323.4 | 3.92 | 6.5 | 82.5 |

[a]Determined by spread plate count method.
[b]Determined with dissolved oxygen meter.

EXAMPLE 2

SOUTH CHARLESTON BIOMASS VIABILITY AS A FUNCTION OF CARBIDE FEED-DEPENDENT RESPIRATION AND TEMPERATURE

| Date | CFU/ml | DIFF OUR (mg O$_2$/l/0.5 min) | MLVSS (g/l) | CFU/gVSS | DIFF OUR[c] (mg O$_2$/gVSS/hr) | Temp. (°C.) |
|---|---|---|---|---|---|---|
| 4/6 | [a]$2.80 \times 10^9$ | 3.72 | 3.82 | $7.33 \times 10^{11}$ | 117 | 17.0 |
| 4/7 | [a]$2.91 \times 10^9$ | 4.16 | 3.88 | $7.50 \times 10^{11}$ | 129 | 17.5 |
| 4/11 | [a]$2.93 \times 10^9$ | 3.95 | 3.84 | $7.63 \times 10^{11}$ | 123 | 19.0 |
| 4/12 | [a]$2.74 \times 10^9$ | 4.05 | 3.76 | $7.27 \times 10^{11}$ | 129 | 20.0 |
| 4/13 | [a]$3.02 \times 10^9$ | 4.04 | 3.80 | $7.95 \times 10^{11}$ | 128 | 21.0 |
| 4/18 | [a]$2.22 \times 10^9$ | 2.30 | 3.86 | $5.75 \times 10^{11}$ | 71.5 | 21.0 |
| 7/11 | [a]$9.50 \times 10^8$ | 1.39 | 3.80 | $2.50 \times 10^{11}$ | 43.9 | 29.0 |
| 10/24 | [a]$1.18 \times 10^9$ | 0.94 | 4.91 | $2.40 \times 10^{11}$ | 23.0 | 20.5 |
| 1/17 | [b]$3.44 \times 10^8$ | 0.93 | 5.45 | $6.31 \times 10^{10}$ | 20.5 | 17.0 |
| 2/22 | [b]$1.49 \times 10^8$ | 0.69 | 5.53 | $2.69 \times 10^{10}$ | 15.0 | 17.0 |

[a]Determined by spread plate colony counts.
[b]Determined by most probable number (MPN) dilution method.
[c]Determined with biological monitor.

EXAMPLE 3

SOUTH CHARLESTON BIOMASS VIABILITY AS A FUNCTION OF CARBIDE FEED-DEPENDENT RESPIRATION

| Date | CFU/ml[a] | DIFF OUR[b] (mg O$_2$/l/hr) | MLVSS (g/l) | CFU/gVSS | DIFF OUR (mg O$_2$/gVSS/hr) |
|---|---|---|---|---|---|
| 12/13 | $2.15 \times 10^9$ | 311.4 | 4.94 | $4.35 \times 10^{11}$ | 63.0 |
| 12/29 | $2.07 \times 10^9$ | 317.6 | 4.56 | $4.54 \times 10^{11}$ | 69.6 |
| 3/8 | $1.54 \times 10^9$ | 290.0 | 4.05 | $3.80 \times 10^{11}$ | 71.6 |
| 4/18 | $2.20 \times 10^9$ | 448.0 | 3.86 | $5.70 \times 10^{11}$ | 116.1 |
| 6/16 | $1.18 \times 10^9$ | 147.4 | 5.64 | $2.09 \times 10^{11}$ | 26.1 |
| 9/1 | $9.93 \times 10^8$ | 196.4 | 5.34 | $1.86 \times 10^{11}$ | 36.8 |

[a]Determined by spread plate colony count method.
[b]Determined with a dissolved oxygen meter.

EXAMPLE 4

INSTITUTE BIOMASS VIABILITY AS A FUNCTION OF INSTITUTE FEED-DEPENDENT RESPIRATION

| Date | CFU/ml[a] | DIFF OUR[b] (mg O$_2$/l/min) | MLVSS (g/l) | CFU/g/VSS | DIFF OUR (mg O$_2$/gVSS/hr) |
|---|---|---|---|---|---|
| 5/25 | $3.29 \times 10^8$ | 2.06 | 2.59 | $1.27 \times 10^{11}$ | 47.8 |
| 6/1 | $3.39 \times 10^8$ | 2.16 | 2.46 | $1.38 \times 10^{11}$ | 52.6 |
| 6/13 | $2.56 \times 10^8$ | 1.74 | 2.72 | $9.42 \times 10^{10}$ | 38.4 |
| 8/8 | $9.50 \times 10^7$ | 0.63 | 2.09 | $4.55 \times 10^{10}$ | 18.1 |
| 7/23 | $2.02 \times 10^8$ | 1.10 | 1.66 | $1.22 \times 10^{11}$ | 39.8 |

[a]Determined by the MPN dilution method.
[b]Institute feed-dependent OUR determined with a dissolved oxygen meter.

As to Example 1: it will be noted that the data for each point were not collected on the same day, which may account for the relatively low correlation coefficient (r=0.88). After the relationship was noted, data for each point were determined on the same day (same sludge sample) in subsequent studies. The correlation coefficient for these later relationships was ≧0.90.

The relationship for Example 1 is: log $CFU/gVSS = 9.50 + 0.024\, DIFF\, OUR$ (mg O$_2$/gVSS/hr referred to on page 7 hereinabove.

As to Example 2: this example provides the data for FIG. 2 of the drawing and, when incorporated with the two additional determinations and temperature dependence, provides the relationship:

$$\log CFU/gVSS = 9.977 + 0.00939 \, DIFF \, OUR + 0.0396 \, TEMP \, (mg \, O_2/gVSS/hr) \, (°C.)$$

As to Example 3: this example employs South Charleston biomass and Carbide Feed. The relationship (from 12/13 to 9/1) is: log $CFU/gVSS + 11.181 + 0.00558$ $DIFF$ $OUR$ (mg $O_2/gVSS/hr$), which is similar to the relationship developed during the period 4/6 to 10/24 with the Biological Monitor, which is: log $CFU/gVSS + 11.280 + 0.00483$ $DIFF$ $OUR$ (mg $O_2/gVSS/hr$ and is shown in FIG. 2.

As to Example 4: this example employs Institute biomass and an Institute Feed. The relationship for this example is: log $CFU/gVSS + 10.427 + 0.0144$ $DIFF$ $OUR$ (mg $O_2/gVSS/hr$).

Composition of synthetic petrochemical reference liquid as to: "Carbide" feed (used in examples 1-3) and "Institute" feed (used in example 4) are as set forth below.

As to the "Carbide" feed, used as the synthetic petrochemical reference liquid for OUR measurement, (in a typical assay) the following components are contained in the 50 ml sample introduced into the measuring vessel (2-liter).

|  | Mg/Vessel |
|---|---|
| Methanol | 44.2 |
| Ethanol | 27.3 |
| Ethylene Glycol | 37.4 |
| Diethylene Glycol | 34.8 |
| Acetic Acid | 21.3 |
| Ethyl Acetate | 27.9 |
| Cyclohexanone | 20.9 |

As to the "Institute" feed, used for synthetic petrochemical reference liquid, (in a typical assay) the following is contained in the 50 ml Sample introduced into the biological monitor vessel (2 liter):

| Acetic Acid | 200 mg |
|---|---|
| Diethylene glycol | 20 mg |
| Methanol | 20 mg |
| Butanol | 20 mg |
| Crotonaldehyde | 3 mg |
| Acetone | 20 mg |

In the data set forth hereinabove, it may be seen that the process of the present invention provides for establishing the linear relationship between the substrate-dependent Oxygen Uptake Rate and the Biomass Viability for each system. As shown in FIG. 2 of the drawing, this relationship can be set forth in curve (linear) form, thereby providing a basis for interpolating and extrapolating viability values corresponding to OUR values for the system in question. Thus, for any given selection of biomass system components, the relationship equation can be easily determined and, as described above, the desired OUR-Viability curve can be plotted and employed for intermediate calculations.

What is claimed is:

1. A method for semi-continuously evaluating the viability of a biomass of a waste treatment basin, said biomass contained in a waste basin mixed liquor, comprising the steps of:
  (a) measuring the rate of oxygen uptake, R, in a first sample of said waste basin mixed liquor, said first sample having a predetermined volume and a predetermined dissolved oxygen content;
  (b) separately measuring the rate of oxygen uptake, M, in a mixture of a second sample of said waste basin mixed liquor and a sample of synthetic petrochemical reference liquid selected to contain organic compounds representative of those normally present in the influent stream passed to the waste basin, said second sample having substantially the same volume and dissolved oxygen content as said first sample, said mixture constituting predominantly said second sample of said waste basin mixed liquor and a relatively small amount of said synthetic petrochemical reference liquid;
  (c) subtracting to determine the differential of said rates, M minus R, which represents the differential oxygen uptake rate of said waste basin mixed liquor in the presence of said synthetic petrochemical reference liquid; and
  (d) effecting, by predetermined correlation with differential oxygen uptake rate, a determination of the viability of said biomass based on said differential oxygen uptake rate for said waste basin mixed liquor.

2. The method in accordance with claim 1, wherein said biomass viability measurement provides a basis for chemical process monitoring and/or control with respect to a waste basin liquor.

3. The method in accordance with claim 2, wherein said biomass viability measurement provides a basis for chemical process monitoring and/or control with respect to an industrial fermentation process.

4. The method in accordance with claim 1, wherein steps (a) and (b) are carried out concurrently.

5. The method in accordance with claim 1, wherein steps (a), (b) and (c) are carried out concurrently.

* * * * *